(12) United States Patent
Jung

(10) Patent No.: US 8,821,919 B2
(45) Date of Patent: *Sep. 2, 2014

(54) WOUND DEBRIDEMENT

(75) Inventor: Steven B. Jung, Rolla, MO (US)

(73) Assignees: Mo/Sci Corporation, Rolla, MO (US); The Curators of the University of Missouri, Columbia, MO (US)

( * ) Notice: Subject to any disclaimer, the term of this patent is extended or adjusted under 35 U.S.C. 154(b) by 47 days.

This patent is subject to a terminal disclaimer.

(21) Appl. No.: 13/475,232

(22) Filed: May 18, 2012

(65) Prior Publication Data

US 2013/0309274 A1 Nov. 21, 2013

(51) Int. Cl.
*A61K 9/70* (2006.01)
*A61P 17/02* (2006.01)

(52) U.S. Cl.
USPC ............................. 424/445; 424/400; 424/447

(58) Field of Classification Search
USPC .......................................... 424/400, 445, 447
See application file for complete search history.

(56) References Cited

U.S. PATENT DOCUMENTS

| | | | |
|---|---|---|---|
| 5,977,428 A | 11/1999 | Bozigian et al. | |
| 6,143,318 A | 11/2000 | Gilchrist et al. | |
| 6,447,805 B1 | 9/2002 | Healy | |
| 6,709,744 B1 | 3/2004 | Day et al. | |
| 6,756,060 B1 | 6/2004 | Greenspan et al. | |
| 7,166,549 B2 | 1/2007 | Fechner et al. | |
| 7,709,027 B2 | 5/2010 | Fechner et al. | |
| 8,173,154 B2 | 5/2012 | Jung et al. | |
| 2004/0166172 A1 | 8/2004 | Rosati et al. | |
| 2004/0170692 A1* | 9/2004 | Day et al. | 424/489 |
| 2004/0253321 A1 | 12/2004 | Fechner et al. | |
| 2005/0169967 A1 | 8/2005 | Gilchrist et al. | |
| 2006/0233887 A1 | 10/2006 | Day | |
| 2007/0020320 A1* | 1/2007 | David et al. | 424/445 |
| 2011/0014261 A1* | 1/2011 | Day et al. | 424/423 |
| 2011/0165221 A1* | 7/2011 | Jung et al. | 424/445 |

FOREIGN PATENT DOCUMENTS

WO 9854104 12/1998

OTHER PUBLICATIONS

Wray, Peter. "Cotton Candy that heals? Borate glass nanofibers look promising." May 11, 2011.*

Kunimoto, Brian. "Managment and Prevention of Venous Leg Ulcers: A Literature Guided Approach." Jun. 2001. Ostomy/Wound Management. vol. 47. Issue 6. pp. 36-49.*

Laplaud et al, "Wound debridement: Comparative reliability of three methods for measuring fibrin percentage in chronic wounds", Wound Repair Regen., Jan.-Feb. 2010 ;18(1):13-20.

Singhal et al., "Options for Nonsurgical Debridement of Necrotic Wounds", Advances in Skin & Wound Care: The Journal for Prevention and Healing, Mar./Apr. 2001, vol. 14, No. 2, p. 96, <http://endoflifecare.tripod.com/ imbeddedlinks/id3.html>.

Dressing Selection Guide by Wound Condition, 2008, 2 pages, <http://www.mhcwoundcare.com/education_resources/Wound_Dressing_Selection_Guide.pdf>.

Shai et al., "Scaled Healing Assessment Index: a novel method for measuring the degree of wound bed preparation", Skin Research and Technology, Aug. 2007, vol. 13, Issue 3, pp. 227-235.

Bryant et al., "Acute and Chronic Wounds: Current Management Concepts", Feb. 2011, Fourth Edition, Chapter 17, p. 279-287.

* cited by examiner

*Primary Examiner* — Frederick Krass
*Assistant Examiner* — Tracy Liu
(74) *Attorney, Agent, or Firm* — Senniger Powers LLP

(57) ABSTRACT

A method for debridement of wound on the skin by placing against the wound a glass-based borate-based composition to release dissolution products which support neutrophilic activity into the wound by dissolution.

26 Claims, 3 Drawing Sheets

93B3 glass; Fiber diameter from ~0.3μm to ~2μm.

WOUND DEBRIDEMENT

FIELD OF THE INVENTION

This invention relates to non-surgical debridement of wounds in mammals.

BACKGROUND OF THE INVENTION

Millions of people are treated for non-healing or slow healing wounds every year. Chronic wounds may have black necrotic eschar, yellow fibrin, and red granulation tissue. Wound debridement refers to processes involving, but not necessarily limited to, removal of the black necrosis and/or yellow fibrin debris from wounds intersecting the skin. For proper and timely healing, these nonviable layers of tissue must to be removed prior to normal wound care management.

Wound debridement is typically performed by standard surgical resection during which the area is anesthetized and the dead tissue is cut way. Surgery can be expensive and traumatic, and presents risks of infection.

U.S. Pat. No. 5,342,352 discloses debridement of eschar by ablating with a laser.

U.S. Pat. No. 7,368,128 discloses debridement via a controlled release dressing providing for controlled release of enzymes from an adsorbent layer such as knitted polyester gauze.

There is a continuing need for new approaches to wound debridement of chronic wounds such as but not limited to lacerations, diabetic ulcers, bed sores, and burns.

SUMMARY OF THE INVENTION

Briefly, therefore, the invention is directed to a method for debridement of a wound on a soft tissue site of a mammalian host comprising placing a first glass-based composition comprising from about 40 to about 90 wt % $B_2O_3$ against an area of the wound comprising non-viable tissue, retaining the first glass-based composition against said area of the wound; replacing the composition by removing the first glass-based composition from against said area of the wound and placing against said area of the wound a subsequent glass-based composition also comprising a glass-based composition comprising from about 40 to about 90 wt % $B_2O_3$; and repeating said replacing and retaining steps so that said retaining is performed cumulatively for a period of at least 24 hours.

Other objects and features of the invention are in part apparent and in part pointed out hereinafter.

DESCRIPTION OF PREFERRED EMBODIMENTS

Figure 1:
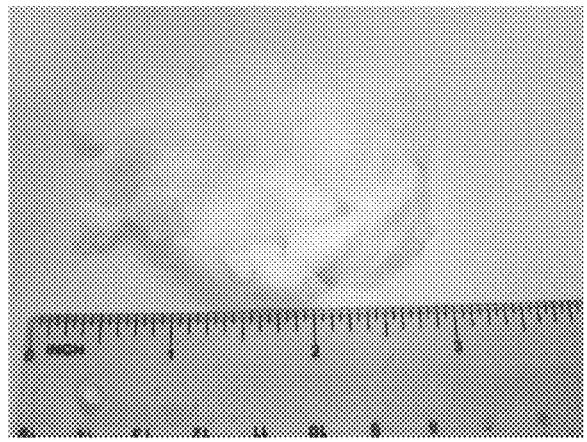
FIG. 1 is a photograph of a three-dimensional compressible body of loose glass-based fibers of the wound care dressing of the invention.

In accordance with this invention, biocompatible and biodegradable glass-based composition containing $B_2O_3$ as the main constituent are employed for wound debridement. In one embodiment, the composition is contained in a dressing to be held in place against an open wound. In another embodiment, the composition is in the form of loose particles or powder that are dusted onto the wound. In another embodiment the composition is particles contained in a liquid vehicle such as water or sterile saline which is sprayed or otherwise coated such as in a slurry onto the wound. The wt % of the particles in the liquid medium is typically between about 0.5 wt % and about 50 wt % particles, for example between about 5 and about 20 wt %.

In another embodiment, the particles are contained in a cream or ointment. The wt % of the particles in the cream or ointment is typically between about 0.5 wt % and about 50 wt % particles, for example between about 5 and about 25 wt %. Petroleum jelly is one example of a suitable cream or ointment. As a general proposition, the particles in these various embodiments have a particle size of between about 0.5 microns and about 150 microns, such as between about 10 and about 50 microns.

The $B_2O_3$-based composition is placed against a wound containing black necrotic eschar and/or yellow fibrin debris. The $B_2O_3$-based composition comprises a glass-based composition comprising from about 40 to about 90 wt % $B_2O_3$, such as between about 40 and about 80 wt % $B_2O_3$. The $B_2O_3$-based composition is retained against the wound such that the glass-based composition releases dissolution products into the wound by dissolution from the composition. The $B_2O_3$-based composition is changed periodically by removing the first wound $B_2O_3$-based composition from against the wound and placing against the wound a subsequent $B_2O_3$-based composition also comprising a glass-based composition comprising from about 40 to about 90 wt % $B_2O_3$, such as from about 40 to about 80 wt % $B_2O_3$. The dissolution products are the elements in the glass such as boron, copper and zinc and they support neutrophil activity. These elements enhance the host's natural neutrophilic activity in the wound area, and raise the neutrophilic activity above normal levels.

In one embodiment, the $B_2O_3$-based composition is a three-dimensional compressible body which is a dressing as described in U.S. Pat. No. 8,173,154 comprising loose biocompatible glass-based fibers comprising from about 40 to about 90 wt % $B_2O_3$, for example from about 40 to about 80 wt % $B_2O_3$. The wound dressing is retained against the wound such that the glass-based fibers release dissolution products into the wound by dissolution from the fibers and particles. In one embodiment, water or saline is applied to the wound dressing such as by dipping prior to placement of the dressing against the wound. This water or saline assists in releasing the dissolution products. In some situations with wet wounds, there is sufficient moisture at the wound itself that the application of water or saline can be omitted.

In alternative embodiments of the method, the $B_2O_3$-based composition takes the form of microspheres, particles, ribbons, flakes, other non-fibrous morphologies, or the like.

In further alternative embodiments, the composition has mixed morphologies, for example a mixture of fibers and particles and/or microspheres.

The $B_2O_3$-based composition is retained against the wound by suitable device. For example, the composition may be retained against the wound by tape, adhesive, incorporation into a wrap or bandage or sleeve, or the like. With the $B_2O_3$-based composition retained against the wound, a primary function is to release dissolution products to the wound. The dissolution products are the elemental components of the glass such boron, copper, zinc, silver, etc.

The composition is changed periodically by removing the composition (i.e., the "first composition" or the "first wound dressing") from against the wound and placing against the wound a subsequent composition such as a subsequent wound dressing. This subsequent composition may also constitute the morphologies described above such as a three-dimensional compressible body comprising loose biocompatible glass-based fibers comprising from about 40 to about 90 wt % $B_2O_3$, such as from about 40 to about 80 wt % $B_2O_3$. The term "subsequent composition" and "subsequent wound dressing" here encompasses third, fourth, fifth, sixth etc. compositions applied over days and weeks during the wound debridement. In one embodiment, the first dressing is retained on the wound for between about 10 hours and seven days before being changed, such as between about 16 hours and about 5 days, for example between 24 and 72 hours. Each subsequent dressing is then, in one embodiment, retained on the wound for a like time period before being changed. Overall, the compositions (cumulatively the first and subsequent compositions) are retained on the wound for a period of at least 24 hours, such as between 24 hours and six weeks, for example between 3 days and 4 weeks.

The wound is preferably cleaned during the changing of the dressing, such as by irrigating with saline, water, or peroxide, or other wound-cleaning procedure as is well understood in the health care field for cleaning a wound between dressing changes.

Figure 3:
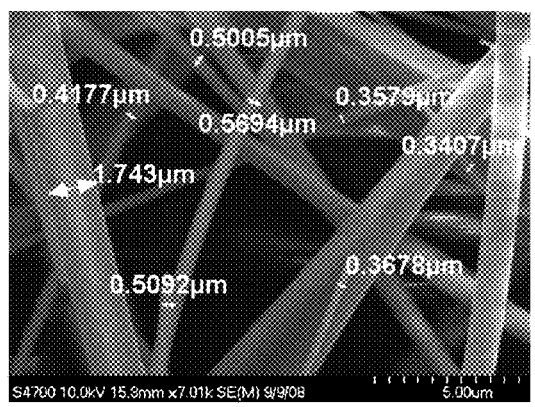
FIG. 3 is a higher magnification SEM image of a body of loose glass-based fibers of the dressing of the invention.

In a first embodiment of the invention, the debridement method of the invention employs a three-dimensional compressible body of loose glass-based fibers such as depicted in FIG. 1, the body comprises fibers having a diameter between about 200 nm (0.2 µm (microns)) and about 4000 nm (4 µm). FIG. 3 is an SEM image of such a body showing various fiber diameters at higher magnification. For example, in one embodiment the fibers have a diameter between about 250 nm (0.25 µm) and about 3000 nm (3 µm), such as between about between about 300 nm (0.2 µm) and about 2000 nm (2 µm). The especially small diameter of these fibers renders them highly flexible so they form into the compressible body without breaking. They have a texture like a cotton ball. In certain embodiments the body consists only of fibers meeting these dimensions, while in other embodiments the body includes fibers meeting these dimensional requirements in addition to other glass morphologies, such as fibers of other dimensions, microspheres, particles, ribbons, flakes or the like. The fibers are generally circular in cross section, but they may be flattish or oval or have other-shaped, non-circular cross section, where cross section is the dimension transverse to the fiber's length. "Diameter" as used herein therefore refers not only to the diameter of a circular cross section, but also to the largest transverse dimension of other, non-circular cross sections.

The number of fibers in the assembly is not narrowly critical to most embodiments, and varies depending on the length of the fibers, size of the dressing, and other factors. For example, in most embodiments, there are hundreds or even thousands of fibers, such as typically at least about 10, at least about 50, or at least about 200 fibers. The upper limit on the number of fibers is dictated by the size of the dressing, and for some embodiments is less than about 50,000, while other embodiments contain more.

Figure 2:
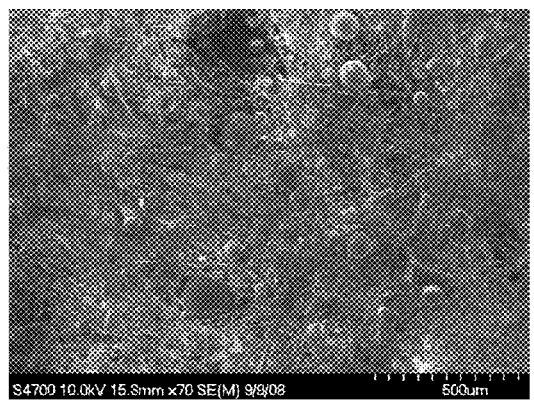
FIG. 2 is a scanning electron microscope (SEM) image of a body of loose glass-based fibers of the invention with glass microspheres interspersed throughout the fibers.

As shown in FIG. 2, the body may also contain, in addition to fine glass fibers, microspheres or beads having a diameter of at least about 10 µm, such as between about 10 µm and about 500 µm, for example between about 20 µm and about 300 µm. In addition to or instead of microspheres, these components may be irregular or regular particles, ribbons, flakes, hollow spheres, or other shapes. While microspheres are preferred in some embodiments, the shape is not narrowly critical in most embodiments, and is to a large extent dictated more by the availability of materials than by other considerations.

The three-dimensional body of glass fibers as a whole has a first state which is unstressed and relaxed when it is in an uncompressed condition such as shown in FIG. 1. The body also has a second state which is stressed when it is in a compressed condition, which generally occurs when the body is shaped and applied to a wound. While the body as a whole is unstressed in its uncompressed condition, the individual fibers are to some extent stressed when they are bent. In the relaxed state, the body has a porosity which is at least about 30% by volume, meaning that at least about 30 vol % of the body is void space not occupied by glass material. For example, in the relaxed state the body is between about 30 vol % and about 90 vol % porosity, such as between about 40 vol % and about 75 vol %. The body may be applied to a wound in an uncompressed state; or it may be compressed so that the porosity is between about 10 vol % and about 75 vol %, such as between about 10 vol % and about 50 vol %. For example, the body may have an uncompressed porosity of between about 40 vol % and 75 vol % and a compressed porosity of between about 10 vol % and about 30 vol %.

The initial surface area of the compressible body varies depending on morphology such as whether it is all fibers, the fiber dimensions, etc. Moreover, the surface area per unit volume changes upon compression, upon application to a wound, and during biodegradation. Generally speaking, a compressible body according to some embodiments of the invention has a surface area/bulk body volume in the relaxed, uncompressed state of the body of between about 1 and about 2000 $cm^{-1}$, such as between about 50 and about 500 $cm^{-1}$.

In the embodiment shown in FIGS. 1 through 3 the fibers are randomly oriented in the body. In alternative embodiments, the fibers may be woven, as may be dictated either by the manner in which the body is formed, or may be dictated by a particular application. For example, in one embodiment the body is in the form of a woven layer which is applied over a wound, similar in morphology to a woven cloth or gauze. The layer may be wrapped around the wound. This layer may constitute the entire dressing, or it may be a component of a multi-component dressing, such as a multilayer dressing. Inasmuch as the layer may constitute the entire dressing, the term "layer" herein is not strictly limited to a layer which is laid over or under another component of the dressing.

The three-dimensional body has a length, width, and thickness. In irregularly shaped embodiments such as shown in FIG. 1, these dimensions refer to the largest or maximum dimensions in each of the x, y, and z directions. For example, the particular embodiment shown in FIG. 1 has a length of about 75 mm (3 inches as shown by the ruler), a width of about 50 mm, and a thickness of about 5 to 25 mm. Generally speaking, the dimensions of the body are dictated by the size of the wounds for which it is applicable. The body therefore typically has an uncompressed length and width of at least about 10 mm, such as between about 10 mm and about 250 mm, for example between about 10 and about 150 mm, between about 10 and about 50 mm, or between about 50 and 200 mm. The body typically has an uncompressed thickness of at least about 2 mm, such as between about 2 and about 100 mm or between about 5 and 30 mm. The body may be manufactured or supplied to the end users or intermediaries in much larger dimensions, and cut to size by the end users or intermediaries.

In those embodiments where the body is in the form of a layer, the thickness is generally much smaller, for example less than 10 mm, such as between about 1 mm and 10 mm. In one embodiment it is between about 1 and about 3 mm thick. The layer may be in the form of a square, for example having a length and width between about 10 and about 300 mm, or in the form of a rectangle having a width between about 10 and about 75 mm and a length between about 50 and about 250 mm. The layer may also be in the form of a roll having a width between about 10 and about 75 mm and a length greater than 25 mm. In some preferred embodiments where the body is a layer, it has a length and a width which are between about 5 and about 30 times the thickness of the body.

In one embodiment the body is subjected to a bonding operation such as sintering which at least lightly bonds the components (fibers and/or particles and/or other morphologies) and converts the body from a flexible body to a non-flexible, rigid body. This yields a non-flexible, rigid dressing for wound debridement comprising a three-dimensional body of bonded glass-based components, for example fibers.

In connection with each of the foregoing embodiments, a trace element such as Ag, Cu, F, Fe, Mn, Mo, Ni, Sr, and Zn, and in some particularly preferred embodiments, Ag, Cu, Sr, Zn, and/or Fe, is preferably incorporated into the glass. Silver has infection-fighting properties. These other elements have an effect on endothelial cell migration which can be useful for blood vessel formation and have importance for tissue regeneration. In this way, these trace elements promote angiogenesis, which is a critical function in promoting tissue growth, such as in wound healing. This is in distinction from promoting osteoconductivity, which refers to providing bone growth factors to a site to promote bone growth. Angiogenesis, which involves increasing vascularity, i.e., vessel growth, is distinct from osteoconductivity.

Companion U.S. Pat. No. 8,173,154 describes using this dressing for wound care in the sense of treating a wound which has typically already been suitably debrided, or which does not require debridement. For wounds that require debridement, there is some overlap between the debridement and the main wound healing process in that during debridement it can be helpful to initiate the angiogenesis process. Accordingly, even though the primary function of the debridement process as described herein is removal of black necrosis eschar and yellow fibrin debris, it can be helpful to include in the glass one or more of the aforementioned trace elements to help initiate angiogenesis in areas not blocked by the eschar and yellow fibrin debris.

In those instances when the one or more trace elements are employed, they are incorporated into the glass in a concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt % (per element). The trace element concentration is typically less than 5 wt %. The trace elements are selected from the group consisting of Ag, Cu, F, Fe, Mn, Mo, Ni, Sr, and Zn. In certain preferred embodiments the trace element is one or more selected from the group consisting of Ag, Cu, Fe, Sr, and Zn. More than one of these trace elements can be employed in a single composition. Also, certain of these elements may be present in greater amounts in that they are not being used as trace elements in accordance with this invention. For example, a glass which contains 0.4 wt % Cu and 15 wt % Sr contains Cu as a trace element in accordance with this invention; and it contains Sr, but not as a trace element in accordance with this invention. Such a material would indeed satisfy the requirement herein for a trace element from the group Ag, Cu, F, Fe, Mn, Mo, Ni, Sr, and Zn in a concentration between about 0.05 and 10 wt % by virtue of the material's Cu content, regardless of its unqualifying Sr content.

Where Cu is desired, the source of Cu to the glass may be a copper oxide such as CuO or $Cu_2O$ or other copper compounds such as copper nitrate or copper sulfate, for example. In one embodiment, Cu is incorporated in a concentration of between about 0.05 and about 5 wt % (about 0.06-6 wt % CuO; about 0.055-5.5 wt % $Cu_2O$), such as between about 0.1 and about 2.5 wt % (about 0.12-3 wt % CuO; about 0.11-3 wt % $Cu_2O$). There are preferred embodiments employing from about 1 wt % to about 2 wt % Cu, as provided by between about 1.2 wt % and about 2.4 wt % CuO.

Where Sr is desired, the source of Sr to the glass may be an oxide such as SrO or other Sr compounds such as $SrCO_3$, for example. In one embodiment, Sr is incorporated in a concentration of between about 0.05 and about 5 wt % (about 0.06 to 5.90 wt % SrO), such as between about 0.1 and about 2.5 wt % (about 0.12 to 2.95 wt % SrO). There are preferred embodiments employing from about 1 wt % to about 2 wt % Sr, as provided by between about 1.18 wt % and about 2.36 wt % SrO.

Where Zn is desired, the source of Zn to the glass may be an oxide such as ZnO or other Zn compounds such as $Zn_3(PO_4)_2$-$xH_2O$, for example. In one embodiment, Zn is incorporated into the glass in a concentration of between about 0.05 and about 5 wt % (about 0.06 to 6.0 wt % ZnO), such as between about 0.1 and about 2.5 wt % (about 0.12 to 3.0 wt % ZnO). There are preferred embodiments employing from about 1 wt % to about 2 wt % Zn, as provided by between about 1.20 wt % and about 2.40 wt % ZnO.

Where Fe is desired, the source of Fe to the glass may be an oxide such as FeO, $Fe_3O_4$, $Fe_2O_3$, or other Fe compounds such as $FeSO_4$-$7H_2O$, for example. In one embodiment, Fe is incorporated into the glass in a concentration of between about 0.05 and about 5 wt % (about 0.06 to 6.45 wt % FeO), such as between about 0.1 and about 2.5 wt % (about 0.13 to 3.23 wt % FeO). There are preferred embodiments employing from about 1 wt % to about 2 wt % Fe, as provided by between about 1.29 wt % and about 2.58 wt % FeO.

Where Ag is desired, the source of Ag to the glass may be $AgNO_3$ or $AgPO_3$, for example. In one embodiment, Ag is incorporated in a concentration of between about 0.05 and about 5 wt %, such as between about 0.1 and about 2.5 wt %.

The glass formers in certain embodiments of the invention are concentration balanced to impart the desired biodegradability. For example, in one embodiment, the concentrations of the glass formers borate, silicate, and phosphate are balanced to 52.95 wt %, 0 wt %, and 4.0 wt %, respectively, with respect to themselves and with respect to the other components in the material $Na_2O$, CaO, and $K_2O$. Balancing in this regard encompasses balancing the concentration of one glass former with other components, such as with those glasses which contain borate and other components, but no phosphate or silicate.

In one embodiment of the invention the glass releases the trace element at particular rate of release of trace element, per gram of glass, per day in a mammalian host. The release rate can in effect be "dialed in" by determining the desired amount of trace element to be released within the host, and then selecting a biocompatible composition or combination of compositions to achieve this rate. As noted above, the glass formers are concentration balanced to impart the desired biodegradability. In a related aspect, the surface area per unit volume can be controlled to control release rate, as greater surface area increases reactivity and therefore release rate. One skilled in the art appreciates that the rate of biodegradation of the glass is different from host to host, from glass to glass, from trace element to trace element, and otherwise depends on a number of factors. For example, a more physically active host with a faster average heart rate may encourage biodegradation and therefore trace element release at a faster rate. In one embodiment, the composition has a trace element release (Cu) rate of between about 0.5 and about 100 E-7 moles of trace element, per gram of glass, per day; for example, between about 1 and about 25 E-7 moles of trace element, per gram of glass, per day; such as between about 1 and about 20 E-7 moles of trace element, per gram of glass, per day, or between about 3 and about 12 E-7 moles of trace element, per gram of glass, per day.

As noted above, the glass inventive bodies and other forms biodegrades or reacts when in contact with physiological fluids. However, in comparison to articles characterized as "water soluble" which dissolve relatively rapidly (over a period of, e.g., 24 hours or less) in aqueous solutions, the biocompatible materials of the invention are not readily soluble in water or aqueous liquids such as physiological liquids, that is, they slowly react with aqueous liquids over a periods of several days to weeks for the fine fibers and generally weeks to months for the microspheres and larger diameter particles. As understood in the art, materials which are "water soluble" are subject to relatively rapid solubility; and materials which are "water insoluble" are either entirely insoluble in water, or are at least only dissolvable with difficulty. Generally speaking the glass employed in the embodiments of this invention are not water insoluble and are not water soluble under this characterization; rather, they are of intermediate water solubility.

The glass material is biocompatible in that it is not toxic or otherwise harmful to its host's living tissue. Some of the preferred compositions (Ca-free) of the invention are also not bioactive, in the sense that hydroxyapatite does not form. That is, they lack bioactivity, where bioactivity refers to a material's capacity in phosphorus-containing mammalian fluids to foster growth of a calcium phosphate layer or convert to bone-precursor calcium phosphate compounds which, in turn, promotes bone bonding to the material.

In one embodiment the glass employed is a borate-based glass material containing the following, approximately, with all percentages herein being by weight, unless stated otherwise:

| | |
|---|---|
| $B_2O_3$ | 40 to 90 |
| $Na_2O$ | 0 to 25 |
| $Li_2O$ | 0 to 25 |
| $K_2O$ | 0 to 25 |
| $Rb_2O$ | 0 to 25 |
| CaO | 0 to 40 |
| MgO | 0 to 25 |
| SrO | 0 to 40 |
| BaO | 0 to 50 |
| $Li_2O + Na_2O + K_2O + Rb_2O$ | 0 to 50 cumulative |
| MgO + SrO + BaO + CaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

The concentrations of $K_2O$ and MgO in certain of these embodiments are each from about 1 to about 25 wt %. In most embodiments, the one or more of $Li_2O$, $Na_2O$, $K_2O$, and $Rb_2O$ is present in a cumulative concentration between about 1 and about 50 wt %, such as between about 5 and about 20 wt %; and the one or more of MgO, SrO, BaO, and CaO is present in a cumulative concentration between about 1 and about 50 wt %, such as between about 5 and about 40 wt %. Where Cu is an optionally included trace element, this composition further contains 0.05 to 5; or 0.01 to 2.5 wt % Cu; as CuO, $Cu_2O$, or other Cu compound. The transition metal elements are those elements where the d-band contains less than its maximum number of ten electrons per atom, and includes, among others, Co and Ni. In fact, certain of the trace elements used in accordance with this invention such as Zn and Fe are transition metals. So in formulations where the trace element concentration of these trace elements is stated to be in a particular range such as between about 0.1 and about 2.5 wt %, of course the trace element concentration is in that range regardless of the fact that transition elements may be among the trace elements, and if Zn and Fe are present in an amount greater than 2.5 wt %, they are not trace elements.

A few exemplary glass materials useful in the invention are as follows:

TABLE 1

Trace-Element-Containing Borate Biocompatible Glasses (wt %)

| Glass | $B_2O_3$ | $Na_2O$ | CaO | $K_2O$ | MgO | $P_2O_5$ | CuO | SrO | ZnO | $Fe_2O_3$ |
|---|---|---|---|---|---|---|---|---|---|---|
| 1550 | 53.0 | 6.0 | 20.0 | 12.0 | 5.0 | 4.0 | | | | |
| 1605 | 51.6 | 6.0 | 20.0 | 12.0 | 5.0 | 4.0 | 0.4 | | 1.0 | |
| 1624 | 51.08 | 5.76 | 19.2 | 11.52 | 4.8 | 3.84 | 0.4 | 2.0 | 1.0 | 0.4 |
| 1662 | 52.5 | 6.0 | 20.0 | 12.0 | 5.0 | 4.0 | | | | 0.5 ($Ag_2O$) |
| 1663 | 51.1 | 6.0 | 20.0 | 12.0 | 5.0 | 4.0 | 0.4 | | | 0.5 ($Ag_2O$) |
| 1 | 52.95 | 5.99 | 19.98 | 11.99 | 5.00 | 4.00 | 0.10 | | | |
| 2 | 52.89 | 5.99 | 19.96 | 11.98 | 4.99 | 3.99 | 0.20 | | | |
| 3 | 52.79 | 5.98 | 19.92 | 11.95 | 4.98 | 3.98 | 0.40 | | | |
| 4 | 52.47 | 5.94 | 19.80 | 11.88 | 4.95 | 3.96 | 1.00 | | | |
| 5 | 51.94 | 5.88 | 19.60 | 11.76 | 4.90 | 3.92 | 2.00 | | | |
| 6 | 51.73 | 5.86 | 19.52 | 11.71 | 4.88 | 3.90 | 0.40 | 2.00 | | |
| 7 | 51.20 | 5.80 | 19.32 | 11.59 | 4.83 | 3.86 | 0.40 | 2.00 | 1.00 | |
| 8 | 50.88 | 5.76 | 19.20 | 11.52 | 4.80 | 3.84 | 0.40 | 2.00 | 1.00 | 0.40 |

In most embodiments the compressible body or glass particles consist only or essentially of components meeting these compositional requirements or other narrower descriptions herein. But generally speaking, for some embodiments other materials not meeting these descriptions may be incorporated.

Additional borate-based materials within this description, into which Ag, Cu or other stated trace element may be incorporated according to this invention, contain, by weight %, the following, keeping in mind that one or more of the other trace elements may be included in addition to Cu in analogous concentrations, or instead of Cu.

TABLE 2

Wt. % Composition of Additional Borate Glasses

| | $B_2O_3$ | $Na_2O$ | $K_2O$ | $Li_2O$ | CaO | BaO | MgO | $P_2O_5$ | CuO |
|---|---|---|---|---|---|---|---|---|---|
| A | 52.5 | 6.0 | 12.0 | | 20.0 | | | 5.0 | 4.0 | 0.5 |
| B | 70.3 | | | 10.3 | 19.3 | | | | 0.1 |
| C | 63.7 | 19.0 | | | 17.2 | | | | 0.1 |
| D | 49.0 | 14.6 | | | | 36.0 | | | 0.4 |
| E | 78.4 | | | 11.5 | 10.0 | | | | 0.1 |
| F | 69.9 | | | 10.0 | 10.0 | 10.0 | | | 0.1 |
| G | 78.6 | | | 11.3 | | | 10.0 | | 0.1 |
| H | 78.6 | | | 11.3 | | 10.0 | | | 0.1 |
| I | 75.9 | | | 11.0 | 13.0 | | | | 0.1 |
| J | 58.6 | | | 8.0 | 33.0 | | | | 0.4 |

It can therefore be appreciated that in addition to the Cu, and/or in addition to Ag, Cu, F, Fe, Mn, Mo, Sr, and/or Zn, the borate-based biocompatible glass materials include 40 to 90 wt % $B_2O_3$ or 40 to 80 wt % $B_2O_3$, such as 50 to 80 wt % $B_2O_3$, or even the narrower $B_2O_3$ ranges described herein, in combination with 1 to 25 wt % $Na_2O$, 1 to 25% $K_2O$, 1 to 40 wt % CaO, 1 to 25 wt % MgO, and 1 to 10 wt % $P_2O_5$. Or the component materials may contain 40 to 80 wt % $B_2O_3$, 1 to 25 wt % $Li_2O$, and 1 to 40 wt % CaO. Or they may contain 40 to 80 wt % $B_2O_3$, 1 to 25 wt % $Na_2O$, and 1 to 40 wt % CaO. Or they may contain 40 to 80 wt % $B_2O_3$, 1 to 25 wt % $Na_2O$, and 1 to 40 wt % BaO. Or they may contain 40 to 80 wt % $B_2O_3$, 1 to 25 wt % $Li_2O$, and 1 to 25 wt % MgO. Or they may contain 40 to 80 wt % $B_2O_3$, 1 to 25 wt % $Li_2O$, and 1 to 40 wt % BaO. While the biocompatible materials hereinabove and hereinbelow are described as containing various oxides by weight %, those skilled in the art understand that in the final glass or glass/crystalline composition, the oxide compounds are dissociated, and the specific oxides, e.g., $B_2O_3$, $SiO_2$, $P_2O_5$, etc. are not separately identifiable or even necessarily separately present. Nonetheless, it is conventional in the art to refer to the final composition as containing a given % of the individual oxides, so that is done here. So from this perspective, the compositions herein are on an equivalent basis.

The biocompatible glass employed in the invention containing the trace element in certain preferred versions are borate-based in that they contain between about 40 and about 90 wt % $B_2O_3$, such as between about 40 and about 80 wt % $B_2O_3$, for example, between about 50 and about 80 wt % $B_2O_3$. Borate-based materials have several important advantages for biological use such as their ease of preparation, ability to be made into glass particulates, microspheres or fibers at relatively low temperatures without crystallization, and, particularly, their biocompatibility. The borate-based materials disclosed herein, compared to silicate-based materials, have significantly faster reaction rates, lower melting temperatures, resistance to crystallization, and in certain instances the absence of silica, which only slowly degrades in the body. So while certain embodiments employ up to about 18 wt % $SiO_2$ in many other preferred embodiments herein, the materials are silicate-free, containing less than 0.1 wt % silicate or even no silicate. In other embodiments, silicate is maintained below 10 wt %, such as below 5 wt %, for example, between 0.5 and 10 wt % or between 0.5 and 5 wt %.

There is one embodiment which has specific preference in certain applications and wherein the concentration of Ca (elemental or in CaO or other compounds) in the glass is controlled to less than about 5 wt %. Certain preferred embodiments strictly control the Ca concentration to less than about 0.5 wt %, such as to less than 0.2 wt %, and even to less than 0.1 wt %. It can be advantageous to avoid Ca for purposes of controlling melt characteristics, such as viscosity, melting temperature, and/or crystallization tendency. The Ca-free compositions lack bioactivity, where bioactivity refers to a material's capacity in phosphorus-containing mammalian fluids to foster growth of a calcium phosphate layer or convert to bone-precursor calcium phosphate compounds.

The biocompatible Ca-free material employed for certain embodiments preferably contains between about 40 and about 90 wt % $B_2O_3$ with the remainder being selected from alkali oxides and alkaline earth oxides, and other optional constituents listed below. For example, this material contains, by weight %:

| | |
|---|---|
| $B_2O_3$ | 40 to 90 |
| $Na_2O$ | 0 to 25 |
| $Li_2O$ | 0 to 25 |
| $K_2O$ | 0 to 25 |
| $Rb_2O$ | 0 to 25 |
| MgO | 0 to 25 |
| SrO | 0 to 40 |
| BaO | 0 to 25 |
| $Li_2O + Na_2O + K_2O + Rb_2O$ | 0 to 50 cumulative |
| MgO + SrO + BaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

In addition, the material optionally contains Cu in a concentration of 0.05 to 5; or 0.01 to 2.5 wt %, as CuO, $Cu_2O$, or other Cu compound, and/or other trace element. Certain of these embodiments contain low levels of Ca, as described above; while others are substantially Ca-free and contain essentially no or less than 0.1 wt % Ca.

In one preferred embodiment, the glass contains between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40% alkaline earth component selected from the group consisting of MgO, SrO, BaO, and combinations thereof. Optional components include $P_2O_5$, $SiO_2$, $Al_2O_3$, F, and transition metal elements. Lanthanides are specifically and strictly excluded from certain preferred embodiments. In some embodiments the biocompatible material consists essentially of between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; between about 5 and about 40 wt % alkaline earth component selected from the group consisting of MgO, SrO, BaO, and combinations thereof, and between about 0.05 and 5 wt % Cu, as CuO, $Cu_2O$, or other Cu compound Exemplary borate-based Ca-free materials, into which Cu may be incorporated according to this invention, contain, by weight %, the following; keeping in mind that one or more of the other trace elements may be included in addition to Cu in analogous concentrations, or instead of Cu:

TABLE 3

Wt. % Composition of Ca-Free Borate Glasses

|   | $B_2O_3$ | $Na_2O$ | $Li_2O$ | MgO | BaO | CuO |
|---|---|---|---|---|---|---|
| I | 49.0 | 14.6 | | | 36.1 | 0.3 |
| II | 78.7 | | 11.1 | 10.0 | | 0.2 |
| III | 78.7 | | 11.1 | | 10.0 | 0.2 |
| IV | 75.8 | | 11.0 | | 13.0 | 0.2 |
| V | 58.7 | | 8.0 | | 33.0 | 0.3 |
| VI | 45.0 | | 6.6 | | 48.0 | 0.4 |
| VII | 69.7 | | 10.0 | 10.0 | 10.0 | 0.3 |

In certain embodiments of the invention, the glass is selected to include at least two of the alkali oxides $Li_2O$, $Na_2O$, $K_2O$, and/or $Rb_2O$ in a cumulative concentration of between about 5 and about 25 wt %, such as between about 8 and 20 wt %. It has been discovered to be advantageous to include two or more such alkali compounds in order to reduce the tendency for crystallization, which ultimately improves the workability and manufacturability of the glasses. Using more than one type of alkali (i.e., mixed alkali) can reduce the cost of a glass, modify its reaction rate with body fluids, and provide additional elements beneficial to tissue growth and regeneration.

A further feature of certain embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %. If SrO is present in a concentration which yields a Sr concentration above 10 wt %, it does not qualify as a trace element in accordance with this description.

These embodiments into which Cu and/or other trace element may be incorporated and which employ mixed alkali oxide contents contain $B_2O_3$ from about 40 to about 80 wt %. Certain of these embodiments consist essentially of $B_2O_3$ from about 40 to about 80 wt %, mixed alkali oxides selected from the group consisting of $Li_2O$, $Na_2O$, $K_2O$, and $Rb_2O$, and one of MgO, SrO, BaO, or CaO, plus the Cu or other trace element compound. Other embodiments consist essentially of $B_2O_3$ from about 40 to about 80 wt %, two or more alkali oxides selected from the group consisting of $Li_2O$, $Na_2O$, $K_2O$, and $Rb_2O$, and two or more alkaline earth oxides from the group consisting of MgO, SrO, BaO, and CaO, plus the Cu or other trace element compound. For example, composition A in Table 2 consists essentially of $B_2O_3$ from about 40 to about 80 wt %, two or more mixed alkali oxides selected from the group consisting of $Li_2O$, $Na_2O$, $K_2O$, and $Rb_2O$ in a cumulative wt % between 5 and 25%, and two or more from among MgO, SrO, BaO, and CaO in a cumulative wt % between 8 and 25%. Other embodiments optionally include one or more of $P_2O_5$, $SiO_2$, $Al_2O_3$, F, and transition metal elements.

The invention includes using fibers or particles from biocompatible glass materials with an especially high $B_2O_3$ composition, namely, from about 60 to about 82 wt %, preferably from about 70 to about 80 wt %. These embodiments employ an alkali oxide selected from the group consisting of $Li_2O$, $Na_2O$, $K_2O$, $Rb_2O$, and combinations thereof cumulatively from about 1 to about 50 wt %, such as from about 5 to about 25 wt %, and even from about 8 to about 20 wt %; and even optionally two or more such oxides cumulatively in this range. They also optionally employ alkaline earth oxides from group consisting of MgO, SrO, BaO, CaO, and combinations thereof in the range of about 1 to about 50 wt %, such as in the range of 1 to 30 wt %, or even about 8 to 25 wt %, and even two or more such oxides cumulatively in this range. Certain of these embodiments consist essentially of these components, such as compositions II, III, IV, and VII in Table 3; while other embodiments optionally include one or more of $P_2O_5$, $SiO_2$, $Al_2O_3$, F, and transition metal elements.

In the foregoing described mixed-alkali and high-borate embodiments, the Ca concentration may be strictly controlled to less than about 5 wt %, including to less than 0.5 wt %, such as to less than 0.2 wt % or less than 0.1 wt %, in the manner discussed above. Alternatively, there are embodiments containing two or more alkali oxides which also contain CaO in an amount up to about 40 wt %.

Some exemplary materials of the invention contain, approximately, 40 to 80 wt % $B_2O_3$, 0.05 to 5% CuO, and $Na_2O$, $K_2O$, MgO, and $P_2O_5$. More specific examples contain or even consist essentially of 40 to 90 wt % $B_2O_3$, 0.1 to 5% CuO, 1 to 25 wt % $Na_2O$, 1 to 25 wt % $K_2O$, 1 to 25 wt % MgO, and 1 to 10 wt % $P_2O_5$.

There is also an option with this invention of employing distinct component compositions to strategically impart certain properties. For example, the debridement device is a compressible body, ointment, cream, or other suitable vehicle which in some embodiments employs 10 to 90 wt % of components having one composition selected from the above, and 10 to 90 wt % of components of a different composition. Or even more than two such types of components may be employed. That is, the material may contain at least 10 wt % of components comprising a first component material within the contemplated compositions and at least 10 wt % of components comprising a second component material, wherein the first and second component materials have compositions distinct from each other. And it is contemplated that only the first component material may contain Cu and/or other trace element. This permits the selection of, for example, faster reacting fibers or particles in combination with slower reacting fibers or particles; or the selection of Ca-containing fibers or particles with Ca-free fibers or particles. One can therefore select standard composition components and combine them with non-standard composition components to effectively customize or dope the overall composition for the application presented, or for the host's particular needs.

The method of making the glass is not narrowly critical to the invention. By way of example, in preparing the glass, individual analytical reagent grade components are weighed, mixed thoroughly, and melted in a platinum crucible at temperatures ranging from 900 to 1500° C. for approximately one to four hours. The melt is then quenched, for example, on a steel or copper plate to form glass that can be ground into particulates of a desired size. The material of preferred compositions when in the form of a melt can easily be formed into fibers or particles. Fibers can either be pulled by hand directly from the melt or pulled through bushing by a rotating drum.

The biocompatible material may be glassy, glass ceramic, or ceramic in nature. However the glassy state is preferred in this invention because, generally speaking, glassy materials are stronger and more chemically homogeneous than their crystalline or partially crystalline counterparts of the same composition. In this description, the term "glass" is used to include materials which are entirely glassy as well as materials which are part glassy and part crystalline. It is therefore preferable that the biocompatible material is substantially glass in that less than about 5 wt %, more preferable less than 1 wt %, of the component material is crystalline material. The glass used in many embodiments of the invention, consistent with the foregoing description, are at least 99 wt % an amorphous or non-crystalline solid, for example made by fusing a mixture of oxides such as one or more of $SiO_2$, $B_2O_3$, $P_2O_5$ (known as glass forming oxides) with basic oxides such as the alkali and alkaline earth oxides, along with the optional one or more trace element compounds such as Cu compounds. In an alternative embodiment, the fibers or particles include glass ceramics fibers that contain both glassy and crystalline regions which in many respects function in the same manner as a fiber that is completely (100%) non-crystalline. The fibers or particles may alternatively be pre-reacted biocompatible glasses such as glass fibers or particles pre-reacted to have a thin surface layer of hydroxyapatite.

EXAMPLE 1

The dressing comprising a compressible body of loose glass-based fibers of FIG. 1 was prepared from glass of composition 53 wt % $B_2O_3$, 20 wt % CaO, 12 wt % $K_2O$, 6 wt % $Na_2O$, 5 wt % MgO, 4 wt % $P_2O_5$. As shown in FIG. 2, there were some residual beads (microspheres) of that are formed as part of the process for forming fibers. The diameter of the fibers ranged from of about 300 nm to about 2000 nm, as shown in FIG. 3. The microspheres were much larger in diameter and ranged from approximately 20 microns to about 300 microns as shown in FIG. 2.

EXAMPLE 2

Figure 4:
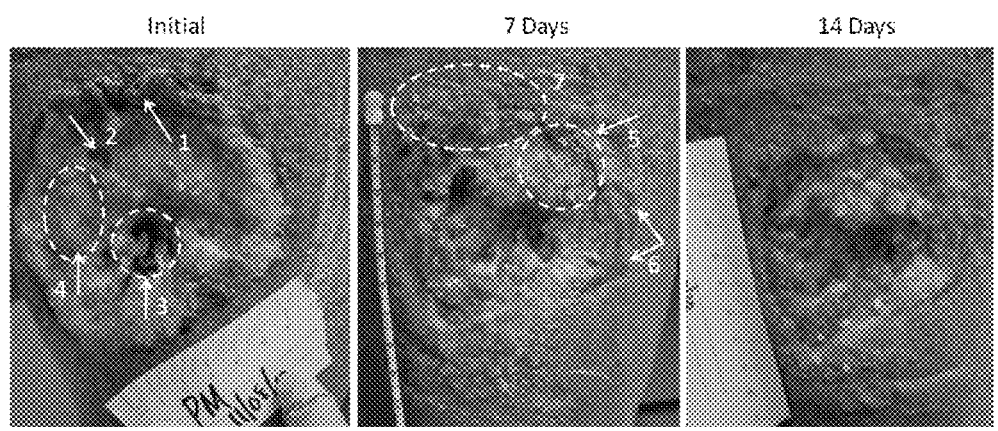
FIGS. 4 and 5 are photographs depicting wound debridement in accordance with the invention and working examples.

A non-healing wound as shown in FIG. 4 containing a hard, non-viable crust treated in accordance with the invention. The dressing used comprised biocompatible fibers and beads having a composition of 51.6 wt % $B_2O_3$, 20 wt % CaO, 12 wt % $K_2O$, 5 wt % MgO, 6 wt % $Na_2O$, 4 wt % $P_2O_5$, 0.4 wt % CuO, and 1.0 wt % ZnO of composition 1605 in Table 1. The fibers were on the order of 500 nm to 5 microns in diameters. In addition to the fibers, the dressing contained about 80-90 wt % of particles (beads) having generally spherical shape. The particles had the same borate-based composition as the fibers.

The dressing was wet with sterile saline and applied against the wound and retained against the wound by a stardard cotton support dressing and wrapped with a compression dressing. The dressing was removed after three to four days, and a new dressing was applied. This removal and application of a new dressing was repeated twice weekly. At each dressing change, the wound was irrigated with sterile saline and re-dressed as describe above.

As can be seen from the figures, the initial wound had non-viable areas of crusty tissue at 1, 2 and 3. The darkness at locations 2 and 3 were thought to be mineralized exudates that would have required surgical debridement. Location 4 showed a thick build-up of wound exudate containing bacteria and fungus, as evident from its potent odor.

After 7 days of this treatment, the odor was significantly reduced, and as shown at location 5, much of the crusty tissue had been removed and replaced with viable tissue. At area 6, the crust which was initially several millimeters thick had been reduced to almost skin level. The thick build-up at 4 had been mostly debrided down to the level of viable tissue. The dark mineralized deposit at area 3 after 7 days was easily flushed away with saline.

After 14 days, the wound had become debrided of the non-viable tissues. The odor was gone, indicating that the bacteria and fungus had been eliminated. The overall inflammation was reduced significantly.

EXAMPLE 3

Figure 5:
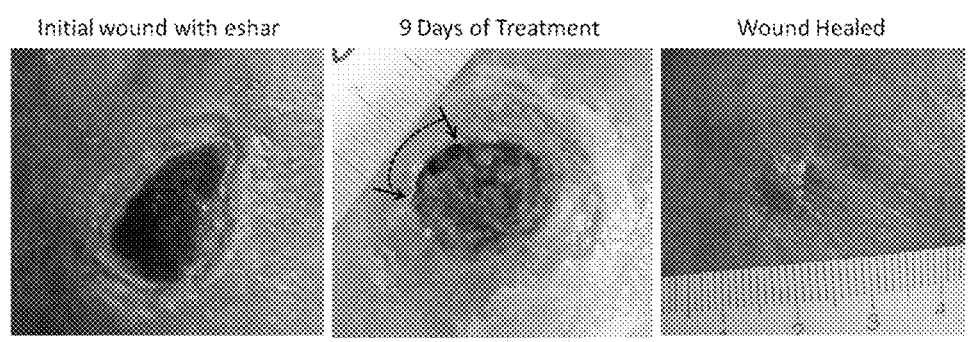

A non-healing wound as shown in FIG. 5 containing a hard black eschar cap was treated in accordance with the Example 2. As can be seen from the figures, the initial wound had a large black eschar cap of the type typically requiring surgical debridement.

After 9 days of this treatment, the eschar was partially dissolved at the edges, and was easily removed with forceps. The removal of the eschar revealed undermining present (arrows) which shows the wound was actually bigger than the topical cover. Once the cover was removed, the wound was able to heal naturally, first filling in the undermined areas, and then epithelializing across the top of the wound. The image on the right shows the fully healed after debridement with the bioactive glass dressing.

EXAMPLE 4

MPO is a marker used to detect and measure neutrophil content. Neutrophilic cells are a subset of leukocytes or white blood cells, the cells that are responsible for acute inflammatory reactions caused by bacteria, viruses, protozoa, pathologic organisms, or other generally injurious occurrence. Chronic wounds that contain the combination of poor blood flow, non-viable tissue, or an infectious agent lack the resources to effectively overcome and heal the wound.

A first wound of a diabetic mouse was treated according to Example 1 with a dressing comprising fibers of the 1605 glass, a second wound of a diabetic mouse was treated according to Example 1 with a dressing of the 1550 glass, and a third (control) wound of a diabetic mouse was left untreated. The MPO content was measured and is presented in FIG. 6.

Figure 6:
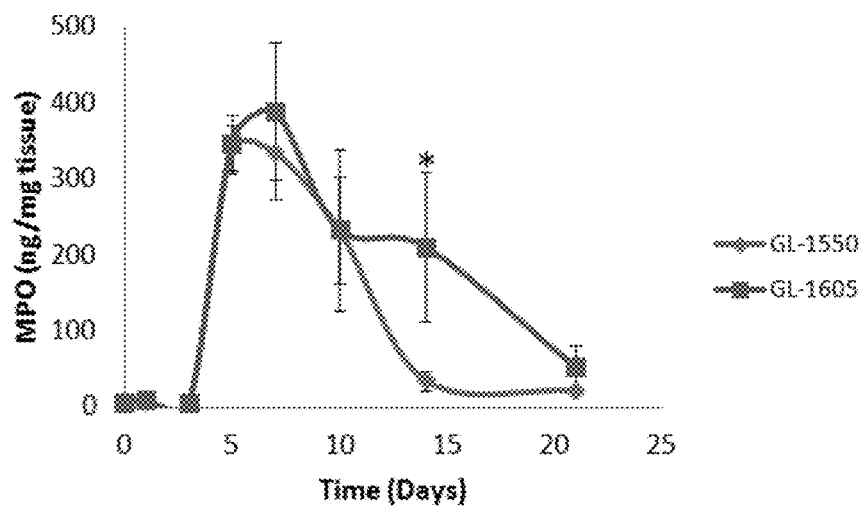
FIGS. 6 and 7 are graphs presenting data generated in accordance with the working examples.

The dissolution products from the 1605 borate glass, doped with copper and zinc, elevated the level of the neutrophilic cells in the adjacent tissue of a diabetic wound and kept the cells in the tissue for an extended and statistically significant period of time (FIG. 6, day 14). This increase in neutrophilic cells or more generally white blood cells is thought to be the reason the debridement is enhanced over the 1550 glass (undoped).

EXAMPLE 5

Figure 7:
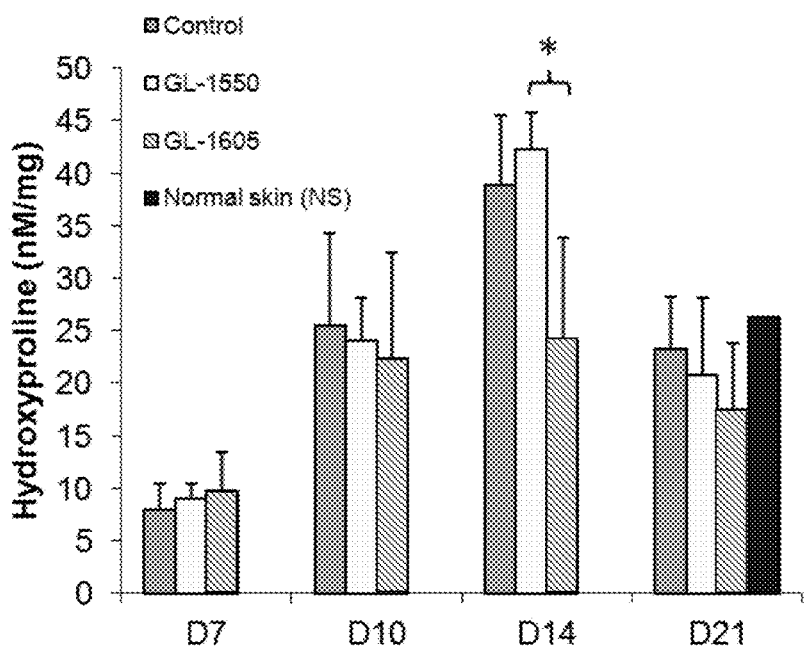

Hydroxyproline content—a measure of the total collagen present in tissue—was also measured in the wounds of the previously mentioned diabetic mouse of Example 4. The data represented by FIG. 7 show that at day 14, the level of total collagen in the wound of Example 4 treated with the 1605 glass is significantly lower than that of the 1550 glass and the control. This decrease in collagen corresponds with the increase in neutrophils shown in FIG. 6. Therefore, the enhanced debridement of non-viable tissue caused an increased level of neutrophils and corresponding delay in the formation of collagen. This delay in collagen formation allows more time for debridement of non-viable tissue which reduces potential scar formation over the long term as a higher quality of regenerated tissue may be formed and will be less likely to re-wound.

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A method for debridement of a wound on a soft tissue site of a mammalian host comprising:
    placing a first glass-based composition comprising from about 40 to about 90 wt % $B_2O_3$ against an area of the wound comprising non-viable tissue comprising black necrotic eschar;
    retaining the first glass-based composition against said area of the wound;
    replacing the composition by removing the first glass-based composition from against said area of the wound and placing against said area of the wound a subsequent glass-based composition also comprising a glass-based composition comprising from about 40 to about 90 wt % $B_2O_3$; and
    repeating said replacing and retaining steps so that said retaining is performed cumulatively for a period of at least 24 hours, said repeating of the replacing and retaining steps resulting in removal of the black necrotic eschar.

2. The method of claim 1 wherein said retaining is performed cumulatively for a period of between 24 hours and six weeks.

3. The method of claim 2 wherein said retaining is performed cumulatively for a period of between three days and four weeks.

4. The method of claim 2 wherein:
    the first glass-based composition and subsequent glass-based compositions constitute dressings of three-dimensional compressible bodies comprising loose biocompatible glass-based fibers comprising the composition comprising about 40 to about 90 wt % $B_2O_3$; and
    at least about 25 wt % of the fibers have a diameter between about 200 nm and about 4000 nm, and a length:diameter aspect ratio of at least about 10.

5. The method of claim 4 wherein the glass-based fibers comprise no more than 18 wt % $SiO_2$.

6. The method of claim 4 wherein the glass-based fibers comprise less than 0.1 wt % $SiO_2$.

7. The method of claim 4 wherein the compressible body in its uncompressed state has a porosity of at least about 30% by volume.

8. The method of claim 4 wherein the compressible body in its uncompressed state has a porosity between 40 and 75 vol. %.

9. The method of claim 4 wherein the body further comprises glass components selected from the group consisting of beads, microspheres, regular particles, irregular particles, ribbons, flakes, and hollow spheres.

10. The method of claim 4 wherein the compressible body has a surface area/bulk body volume in the relaxed, uncompressed state of the body of between about 1 and about 2000 $cm^{-1}$.

11. The method of claim 4 wherein the compressible body has a surface area/bulk body volume in the relaxed, uncompressed state of the body of between about 50 and about 500 $cm^{-1}$.

12. The method of claim 4 wherein the glass-based fibers further comprise one or more trace elements selected from the group consisting of Ag, Cu, F, Fe, Mn, Mo, Ni, Sr, and Zn in a concentration between about 0.05 and 10 wt % per trace element chemically dissolved in the biocompatible fibers.

13. The method of claim 12 wherein the one or more trace elements are homogeneously dispersed within the fibers and are thereby adapted to be time-released during biodegradation of said fibers.

14. The method of claim 2 wherein the glass-based compositions release dissolution products which support neutrophilic activity into the wound by dissolution from the compositions.

15. The method of claim 4 wherein:
    the dressings are three-dimensional compressible bodies comprising loose biocompatible glass-based fibers comprising the composition comprising about 40 to about 90 wt % $B_2O_3$;
    at least about 25 wt % of the fibers have a diameter between about 200 nm and about 4000 nm, and a length:diameter aspect ratio of at least about 10;
    the glass-based fibers comprise 50 to 80 wt % $B_2O_3$, 1 to 25 wt % $Na_2O$, 1 to 25% $K_2O$ wt %, 1 to 40 wt % CaO, 1 to 25 wt % MgO, and 1 to 10 wt % $P_2O_5$.

16. The method of claim 15 wherein the glass-based fibers further comprise a biocompatible material which comprises one or more trace elements selected from the group consisting of Ag, Cu, F, Fe, Mn, Mo, Ni, Sr, and Zn in a concentration between about 0.05 and 10 wt % per trace element chemically dissolved in the biocompatible material.

17. The method of claim 4 wherein the glass-based fibers consist essentially of 50 to 80 wt % $B_2O_3$, 1 to 25 wt % $Na_2O$, 1 to 25% $K_2O$, 1 to 40 wt % CaO, 1 to 25 wt % MgO, and 1 to 10 wt % $P_2O_5$.

18. The method of claim 4 wherein the glass-based fibers comprise 50 to 80 wt % $B_2O_3$, 1 to 25 wt % $Na_2O$, 1 to 25% $K_2O$, 1 to 40 wt % CaO, 1 to 25 wt % MgO, 1 to 10 wt % $P_2O_5$, Cu compounds to provide an equivalent of between 0.05 and 5 wt % Cu, and Zn compounds to provide an equivalent of between 0.05 and 5 wt % Zn.

19. The method of claim 4 wherein the glass-based fibers consist essentially of 51.6 wt % $B_2O_3$, 20 wt % CaO, 12 wt % $K_2O$, 5 wt % MgO, 6 wt % $Na_2O$, 4 wt % $P_2O_5$, 0.4 wt % CuO, and 1.0 wt % ZnO.

20. The method of claim 2 wherein:
    the first glass-based composition and subsequent glass-based compositions constitute dressings of three-dimensional compressible bodies comprising biocompatible glass-based fibers comprising the composition and the composition comprises 50 to 80 wt % $B_2O_3$, 1 to 25 wt % $Na_2O$, 1 to 25% $K_2O$, 1 to 40 wt % CaO, 1 to 25 wt % MgO, and 1 to 10 wt % $P_2O_5$.

21. The method of claim 2 wherein:
    each of the glass-based compositions is in the form of a dressing which is a flexible three-dimensional compressible body of loose glass-based fibers comprising the composition of from about 40 to about 90 wt % $B_2O_3$;
    at least about 25 wt % of the fibers have a diameter between about 200 nm and about 4000 nm, and a length:diameter aspect ratio of at least about 10;
    the glass-based fibers comprise a biocompatible material which comprises one or more trace elements selected from the group consisting of Ag, Cu, F, Fe, Mn, Mo, Ni, Sr, and Zn in a concentration between about 0.05 and 10 wt % per trace element chemically dissolved in the biocompatible material;

the compressible body is a layer having a length and a width which are between about 5 and about 30 times the thickness of the body; and wherein the layer is woven.

22. The method of claim 2 wherein the glass-based compositions are in a cream or ointment.

23. The method of claim 2 wherein the glass-based compositions are in a liquid medium.

24. The method of claim 2 wherein the glass-based compositions are in the form of components bonded into a rigid formation.

25. The method of claim 1 wherein the glass-based compositions are in a wound dressing and the wound dressing is wet with saline or water prior to placing the compositions against the wound.

26. The method of claim 2 wherein the glass-based compositions are in a wound dressing and the wound dressing is wet with saline or water prior to placing the compositions against the wound.

* * * * *